United States Patent [19]

Baltz et al.

[11] 4,321,362

[45] Mar. 23, 1982

[54] DE(MYCINOSYLOXY)TYLOSIN AND PROCESS FOR ITS PRODUCTION

[75] Inventors: Richard H. Baltz; Gene M. Wild, both of Indianapolis, Ind.; Eugene T. Seno, Norwich, England

[73] Assignee: Eli Lilly and Company, Indianapolis, Ind.

[21] Appl. No.: 156,855

[22] Filed: Jun. 12, 1980

[51] Int. Cl.$^3$ .................... A61K 31/71; C07H 17/08
[52] U.S. Cl. .................... 536/17 R; 424/180; 435/76
[58] Field of Search ........ 536/9, 17 R, 17 C

[56] References Cited

U.S. PATENT DOCUMENTS

| | | | |
|---|---|---|---|
| 3,178,341 | 4/1965 | Hamill et al. | 424/180 |
| 3,326,759 | 6/1967 | Hamill et al. | 424/180 |
| 3,344,024 | 9/1967 | Whaley et al. | 424/180 |
| 3,459,853 | 8/1969 | Gorman et al. | 424/180 |
| 3,923,784 | 12/1975 | Kierstead et al. | 536/9 |
| 3,939,144 | 2/1976 | Radobolja et al. | 536/9 |
| 4,056,616 | 11/1977 | Reimann et al. | 536/17 R |
| 4,161,523 | 7/1979 | Weinstein et al. | 536/17 R |
| 4,196,280 | 4/1980 | Umezawa et al. | 536/17 R |
| 4,205,163 | 5/1980 | Mori et al. | 536/17 R |

OTHER PUBLICATIONS

A. Kinumaki et al., "J. Antibiotics", vol. 30, No. 6, pp. 450-454, 1977.
Tanabe Pharmaceuticals, Japanese Examined Pat. No. 6037-351 (Derwent Abstract 86252x/46 only).
Yamaguchi et al., "J. Antibiotics", vol. 31, No. 5, pp. 433-440, 1978.
Tanabe Pharmaceuticals, Japanese Examined Pat. No. 6037-352 (Derwent Abstract 86253x/46 only).
Tsukiura et al., "J. Antibiotics", vol. 22, No. 3, pp. 89-99, 1969.
Suzuki et al., "Chem. Letters", 1973, pp. 793-798.
Nash et al., "Current Chemotherapy & Infectious Disease Proc. of 11th ICC & 19th ICAAC., Amer. Soc. of Microbiology", pp. 462-463, 1980.
Nagel et al., "J. Org. Chemistry", 44 #12, pp. 2050-2052, 1979.
Masamune et al., "J. Amer. Chem. Soc.", 98 #24, pp. 7874-7875, 1976.
Okamoto et al., "Japanese Kokai Tokyo Koho" 80; 43,0183 (abstract from Chem. Abst. vol. 93, 68663u (1980) only).

Primary Examiner—Johnnie R. Brown
Attorney, Agent, or Firm—Nancy J. Harrison; Arthur R. Whale

[57] ABSTRACT

23-De(mycinosyloxy)tylosin (DMOT) which has the formula:

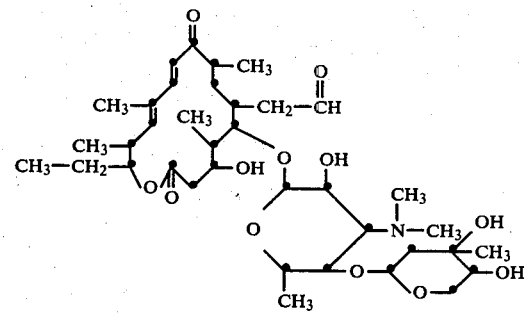

20-dihydro-DMOT, specified acyl ester derivatives, and the acid addition salts thereof are useful antibacterial agents. New methods of making 23-deoxy-5-O-mycaminosyltylonolide (DOMT) and 20-dihydro-DOMT by mild acid hydrolysis of DMOT and 20-dihydro-DMOT, respectively, are included.

15 Claims, 1 Drawing Figure

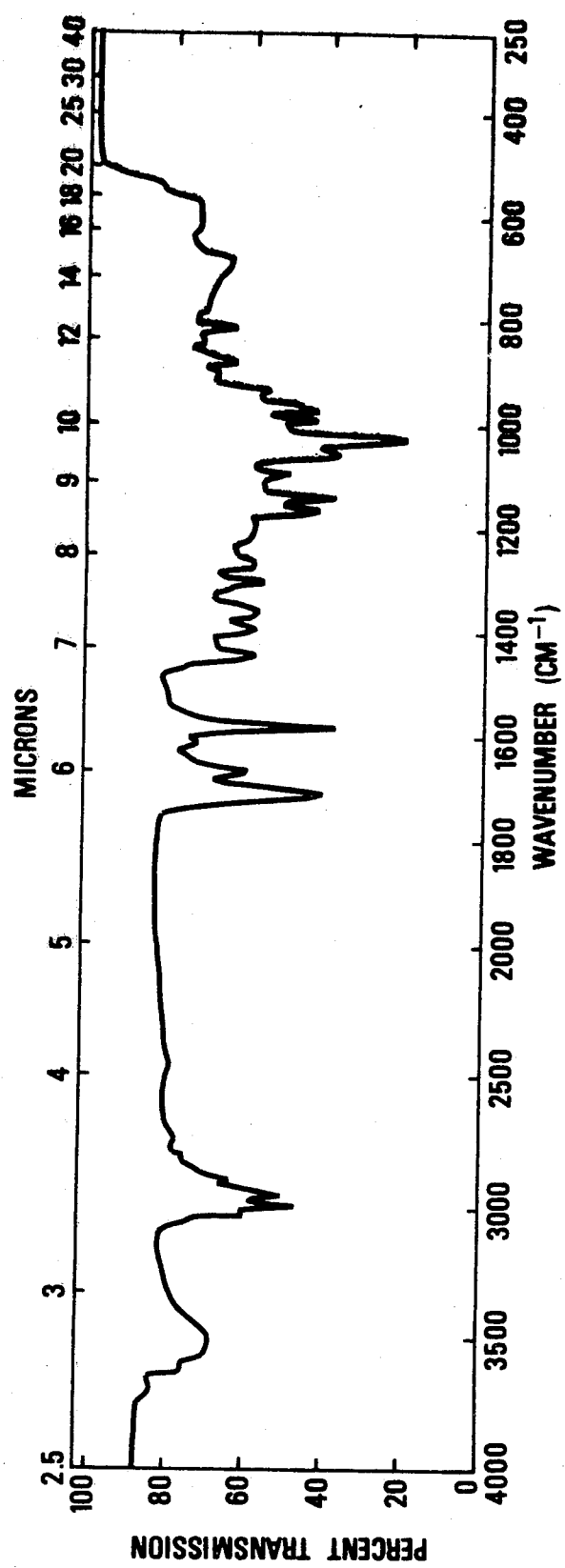

DE(MYCINOSYLOXY)TYLOSIN AND PROCESS FOR ITS PRODUCTION

SUMMARY OF THE INVENTION

This invention relates to a new macrolide antibiotic, 23-de(mycinosyloxy)tylosin, and to its 20-dihydro derivative. 23-De(mycinosyloxy)tylosin, which will be called de(mycinosyloxy)tylosin or DMOT for convenience herein, has structure 1:

*[Chemical structure 1]*

Although no stereochemical assignments are indicated in the structures given herein, the stereochemistry of the compounds is identical to that of tylosin. The neutral sugar in structure 1 is mycarose, and the aminosugar in 1 is mycaminose. The dihydro-derivative of DMOT, i.e. 20-dihydro-23-de(mycinosyloxy)tylosin, will be called dihydro-DMOT for convenience herein. Dihydro-DMOT has structure 2:

*[Chemical structure 2]*

DMOT and dihydro-DMOT inhibit the growth of organisms which are pathogenic to animals. More specifically, they are antibacterial agents which are especially active against gram-positive microorganisms and Mycoplasma species.

The hydroxyl groups of DMOT and dihydro-DMOT can be esterified on the 2′, 4″, 3″ and 3-hydroxyl groups to form useful acyl ester derivatives. In addition, dihydro-DMOT can be esterified on the 20-hydroxyl group. Esterification of the 2′-hydroxyl group is most facile.

Typical esters are those of a monocarboxylic acid or hemi-esters of a dicarboxylic acid having from 2 to 18 carbon atoms.

DMOT, dihydro-DMOT and their acyl ester derivatives are basic compounds which, when treated with acids, are converted to acid addition salts. These addition salts are also part of this invention. To simplify discussions of utility, the term "DMOT compound" is used and refers to DMOT, dihydro-DMOT, a specified acyl ester derivative of these compounds, or a pharmaceutically acceptable acid addition salt of DMOT, dihydro-DMOT or of their acyl ester derivatives.

This invention further relates to a new strain of *Streptomyces fradiae*, NRRL 12171, and to the method of producing DMOT or dihydro-DMOT by culturing this strain under submerged aerobic fermentation conditions until a substantial level of antibiotic activity is produced. DMOT or dihydro-DMOT can be extracted from basified broth filtrate with polar organic solvents and can be further purified by adsorptive or extractive procedures.

This invention also relates to a new method of preparing 23-deoxy-5-O-mycaminosyltylonolide (abbreviated herein as DOMT) and 20-dihydro-23-deoxy-5-O-mycaminosyltylonolide (dihydro-DOMT) by mild acid hydrolysis of DMOT or dihydro-DMOT, respectively. DOMT has structure 3:

[Chemical structure diagram of DOMT, formula 3]

DESCRIPTION OF THE DRAWING

The infrared absorption spectrum of DMOT (free base) in chloroform is presented in the accompanying drawing.

DETAILED DESCRIPTION

The following paragraphs describe the properties of DMOT.

DMOT

The structure of DMOT is shown in formula 1. DMOT is a white amorphous solid which softens at about 158° and melts at about 165°–167° C. Elemental analysis indicates that it has the following approximate percentage composition: carbon, 62%; hydrogen, 8%; nitrogen, 2%; oxygen, 27%. It has an empirical formula of $C_{38}H_{63}NO_{12}$ and a molecular weight of about 726 (725 as determined by mass spectrometry).

The infrared absorption spectrum of DMOT (free base) in chloroform is shown in the accompanying drawing. Observable absorption maxima occur at the following frequencies ($cm^{-1}$): 3653 (small), 3588 (shoulder), 3470 (broad), 3026 (shoulder), 2998 (shoulder), 2969 (intense), 2932 (intense), 2873 (shoulder), 1709 (intense), 1669 (medium), 1616 (v. small), 1583 (intense), 1447 (medium), 1400 (medium), 1364 (medium), 1309 (medium), 1278 (small), 1175 (medium), 1151 (medium), 1106 (small), 1066 (shoulder), 1036 (intense), 1001 (medium), 982 (medium), 972 (shoulder), 946 (small), 913 (v. small), 891 (v. small), 853 (v. small), 826 (small).

The ultraviolet absorption spectrum of DMOT in neutral ethanol exhibits an absorption maximum at 283 nm ($\epsilon$ 21,500).

DMOT (free base) has the following specific rotation: $[\alpha]_D^{25} -62.75°$ (c 1, $CH_3OH$).

Electrometric titration of DMOT in 66% aqueous dimethylformamide indicates the presence of a titratable group with a $pK_a$ value of about 7.3.

DMOT free base is sparingly soluble in water, but is soluble in most popular organic solvents, such as acetone, methanol, ethanol, dimethylformamide, chloroform and dimethyl sulfoxide. DMOT acid addition salts are more soluble in water than is DMOT base.

DMOT can be distinguished from tylosin and from DOMT by paper and thin-layer chromatography. The approximate Rf and Rx values of these antibiotics are summarized in Tables 1 and 2. In Table 2 Rx value is the ratio of movement expressed relative to that of tylosin, which was given a value of 1.0. Bioautography with *Bacillus subtilis* was used for detection.

TABLE 1

| | Thin-Layer Chromatography of $DMOT^a$ | | |
|---|---|---|---|
| | | Rf Value | |
| Compound | $A^b$ | B | C |
| Tylosin | 0.53 | 0.53 | 0.67 |
| DMOT | 0.70 | 0.56 | 0.67 |
| DOMT | 0.48 | 0.17 | 0.24 |

[a] Medium: Merck, Darmstadt - Silica Gel 60
[b] Solvent:
A = ethyl acetate:diethylamine (96:4)
B = acetone:ethanol (2:1)
C = chloroform:methanol (3:1)

TABLE 2

| | Paper Chromatography of $DMOT^a$ | |
|---|---|---|
| | Rx | |
| Compound | $D^b$ | E |
| Tylosin | 1.00 | 1.00 |
| DMOT | 1.50 | 1.09 |
| DOMT | 0.50 | 0.97 |

[a] Paper: Whatman No. 1 treated with 0.75 M $KH_2PO_4$ buffer at pH 4.0 and dried
[b] Solvent:
D = ethyl acetate saturated with water
E = n-butanol saturated with water

Dihydro-DMOT

Dihydro-DMOT can be obtained by chemical reduction or by fermentation. When preparing dihydro-DMOT by chemical reduction, known procedures such as, for example, treatment with an approximately stoichiometric amount of sodium borohydride in an alcoholic solvent, may be used. Dihydro-DMOT is also produced by the *S. fradiae* NRRL 12171 of this invention under controlled fermentation conditions.

Ester Derivatives

DMOT and dihydro-DMOT can be esterified at the 2′, 4″, 3″ and 3-positions to give acyl ester derivatives by treatment with acylating agents using methods known in the art. In addition, dihydro-DMOT can be esterified at the 20-position. Esterification of the 2′-hydroxyl group is most facile. Typical acylating agents include anhydrides, halides (usually in combination with a base or other acid scavenger) and active esters of organic acids. Acylation can also be achieved by using a mixture of an organic acid and a dehydrating agent such as N,N′-dicyclohexylcarbodiimide. Acylations can also be carried out enzymatically as described by Okamoto et al. in U.S. Pat. No. 4,092,473. Once formed, the acyl derivatives can be separated and purified by known techniques.

The 2′-monoester derivatives can be prepared by selective esterification techniques generally known in the art, such as, for example, treatment of the antibiotic with a stoichiometric quantity (or a slight excess) of an acylating agent, such as an acyl anhydride, at about room temperature for from about 1 to about 24 hours until esterification is substantially complete. The 2′-monoester can be isolated from the reaction mixture by standard procedures such as extraction, chromatography and crystallization.

Useful esters are those of organic acids including aliphatic, cycloaliphatic, aryl, aralkyl, heterocyclic carboxylic, sulfonic and alkoxycarbonic acids of from 2 to 18 carbon atoms, and of inorganic acids, such as sulfuric and phosphoric acids.

Representative suitable esters include those derived from acids such as acetic, chloroacetic, propionic, butyric, isovaleric, alkoxycarbonic, stearic, cyclopropanecarboxylic, cyclohexanecarboxylic, β-cyclohexylpropionic, 1-adamantanecarboxylic, benzoic, phenylacetic, phenoxyacetic, mandelic and 2-thienylacetic acids, and alkyl-, aryl-, and aralkyl-sulfonic acids, the aryl- and aralkyl- acids optionally bearing substituents such as halogen, nitro, lower alkoxy and the like on the aromatic moiety. Suitable esters also include hemi-esters derived from dicarboxylic acids such as succinic, maleic, fumaric, malonic and phthalic acids.

Pharmaceutically acceptable ester derivatives are a preferred group. Other ester derivatives are useful, however, as intermediates.

Salts

DMOT, dihydro-DMOT and their specified acyl derivatives form acid addition salts. The acid addition salts of DMOT, dihydro-DMOT and of their acyl derivatives are also part of this invention. Such salts are useful, for example, for separating and purifying DMOT, dihydro-DMOT and their acyl derivatives. In addition the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts are an especially preferred group of salts of this invention. "Pharmaceutically acceptable" salts are salts in which the toxicity of the compound as a whole toward warm-blooded animals is not increased relative to the non-salt form.

Preparation of DOMT and Dihydro-DOMT

This invention also relates to new methods of preparing 23-deoxy-5-O-mycaminosyltylonolide (3) (DOMT) and dihydro-DOMT by mild acid hydrolysis of DMOT and dihydro-DMOT, respectively. Mild acid hydrolysis conditions are known in the art. Appropriate solutions having a pH of about four or below can be used to accomplish the hydrolysis. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating either DMOT or dihydro-DMOT with a mild acid solution for a time sufficient to effect removal of the mycarosyl group to give DOMT or dihydro-DOMT, respectively.

Alternatively, and sometimes preferably, DOMT or dihydro-DOMT can be prepared by treating DMOT or dihydro-DMOT in the fermentation broth in which it is produced, using mild acidic conditions as above described for a time sufficient to convert the DMOT or dihydro-DMOT or DOMT or dihydro-DOMT, respectively. DOMT or dihydro-DOMT thus prepared can be isolated from the fermentation broth using techniques known in the art.

DOMT is identical to depoxycirramycin $A_1$ (de-epoxycirramycin $A_1$). The preparation and activity of depoxycirramycin $A_1$ are described by H. Tsukiura et al. in J. Antiobiotics 22 (3), 89–99, and 100–105 (1969). Tsukiura et al. prepare depoxycirramycin $A_1$ by treating cirramycin $A_1$ with potassium iodide in acetic acid.

Another potential method of making DOMT is suggested by T. Suzuki et al. in Chemistry Letters 1973, 793–798. This method involves treating antibiotic B-58941 with potassium iodide in acetic acid to obtain a product which "may be identical with depoxycirramycin $A_1$". DOMT is also related to M-4365 $G_2$ (repromicin) and rosamicin, being 4'-hydroxy-M-4365 $G_2$ or de-epoxy-4'-hydroxy-rosamicin, respectively [see A. Kinumaki et al., J. Antibiotics 30 (6), 450–454 (1977)]. Preparation of DOMT from either M-4365 $G_2$ or rosamicin, however, would be impractical.

Preparation of DMOT and Dihydro-DMOT by S. fradiae.

DMOT and dihydro-DMOT are prepared by culturing a strain of Streptomyces fradiae which produces these compounds under submerged aerobic conditions in a suitable culture medium until substantial antibiotic activity is produced. As will be appreciated by those skilled in the art, DMOT is produced first in the fermentation process. Dihydro-DMOT is produced when the fermentation is carried out for a longer time, thus permitting the DMOT present to be reduced enzymatically.

The culture medium used to grow Streptomyces fradiae NRRL 12171 can be any one of a number of media. For economy in production, optimal yield, and ease of product isolation, however, certain culture media are preferred. Thus, for example, preferred carbon sources in large-scale fermentation include carbohydrates such as dextrin, glucose, starch, and corn meal and oils such as soybean oil. Preferred nitrogen sources include corn meal, soybean meal, fish meal, amino acids and the like. Among the nutrient inorganic salts which can be incorporated in the culture media are the customary soluble salts capable of yielding iron, potassium, sodium, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism. It may be necessary to add small amounts (i.e. 0.2 ml/L) of an antifoam agent such as polypropylene glycol (M.W. about 2000) to large-scale fermentation media if foaming becomes a problem.

For production of substantial quantities of DMOT or dihydro-DMOT, submerged aerobic fermentation in tanks is preferred. Small quantities of DMOT or dihydro-DMOT may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the vegetative inoculum can be the same as that used for larger fermentations, but other media can also be used.

S. fradiae NRRL 12171 can be grown at temperatures between about 10° and about 37° C. Optimum antibiotic production appears to occur at temperatures of about 28° C.

As is customary in aerobic submerged culture processes, sterile air is bubbled through the culture medium. For efficient antibiotic production the percent of air saturation for tank production should be about 30% or above (at 28° C. and one atmosphere of pressure).

Antibiotic production can be followed during the fermentation by testing samples of the broth against organisms known to be sensitive to these antibiotics. One useful assay organism is *Staphylococcus aureus* ATCC 9144. The bioassay is conveniently performed by an automated turbidometric method. In addition, antibiotic production can be readily monitored by high-performance liquid chromatography with UV detection.

Following its production under submerged aerobic fermentation conditions, DMOT or dihydro-DMOT can be recovered from the fermentation medium by methods used in the fermentation art. Recovery of DMOT or dihydro-DMOT is accomplished by an initial filtration of the fermentation broth. The filtered broth can then be further purified to give the desired antibiotic. A variety of techniques may be used in this purification. A preferred technique for purification of the filtered broth involves adjusting the broth to about pH 9; extracting the broth with a suitable solvent such as ethyl acetate, amyl acetate or methyl isobutyl ketone; extracting the organic phase with an aqueous acidic solution; and precipitating the antibiotic by making the aqueous extract basic. Further purification involves the use of extraction, adsorption and/or precipitation techniques.

The Microorganism

The new microorganism of this invention was obtained by chemical mutagenesis of a *Streptomyces fradiae* strain which produced tylosin. The microorganism obtained by mutagenesis produces only minimal amounts of tylosin, but produces DMOT as a major component.

For characterization purposes, the new organism was compared with *Streptomyces fradiae* strain M48-E 2724.1, a tylosin-producing strain derived from *S. fradiae* NRRL 2702.. *S. fradiae* NRRL 2702 was disclosed by Hamill et al. in U.S. Pat. No. 3,178,341, issued Apr. 13, 1965. In the discussions herein the tylosin-producing *S. fradiae* M48-E 2724.1 culture will be called "E2724.1".

The new strain which produces DMOT and dihydro-DMOT, NRRL 12171, is also classified as a strain of *Streptomyces fradiae*. In characterizing this organism, the methods recommended for the International Streptomyces Project for the characterization of Streptomyces species have been followed [E. B. Shirling and D. Gottlieb, "Methods For Characterization of Streptomyces Species," *Internal. Journal of Systematic Bacteriology*, 16 (3), 313–340 (1966)] along with certain supplementary tests. The following references to *S. fradiae* in the literature were consulted: (1) R. E. Buchanan and N. E. Gibbons, "Bergey's Manual of Determinative Bacteriology," 8th ed., The Williams and Wilkins Co., Baltimore, Md., 1974, p. 815; and (2) E. B. Shirling and D. Gottlieb, "Cooperative Description of Streptomyces. II. Species Description from First Study," *Internal. Journal of Systematic Bacteriology*, 18 (2), 118, (1968).

The following description of the strain which produces DMOT compares its characteristics with those of the tylosin-producing *S. fradiae* strain "E2724.1".

Characterization of the Microorganism

The spore-chain morphology of the new strain and of the E2724.1 strain is in the Retinaculum-Apertum (RA) section. Hooks, loops, and irregular coils are short and generally not of a wide diameter. This is best observed on ISP#2 (yeast-malt extract agar) for strain E2724.1 and on Czapek's solution agar for the new strain. The spore surface is smooth; the spore shape is spherical with an average size of 0.65 $\mu$M in diameter. The diameter range is from 0.61 to 0.71 $\mu$M.

The most obvious differences between these strains are seen in their cultural characteristics. The E2724.1 strain produces aerial mycelia fairly well on most media and is in the White color series. The new strain of this invention produces very little if any aerial mycelia. When present, it is in the White to Gray color series. The reverse sides of these colonies have no distinctive pigments produced. They are light to moderate yellow in color. Melanoid pigment production is negative[1].

[1] Melanoid-pigment production was tested using ISP#1 (tryptone-yeast extract broth), ISP#6 (peptone yeast extract-iron agar), ISP#7 (tyrosine agar), and ISP#7 agar without tyrosine.

A summary of the important similarities and differences between the E2724.1 strain and the new strain of this invention is given in Table 3.

TABLE 3

| Comparison of *Streptomyces fradiae* E 2724.1 and NRRL 12171 | |
|---|---|
| Similarities | Differences |
| Spore-chain morphology | Cultural characteristics |
| Spore-surface ornamentation | NaCl tolerance |
| Spore size | pH range |
| Lack of chromogenicity | Temperature range |
| Lack of soluble pigments | |
| Growth in selected vegetative media | |
| Starch hydrolysis | |
| Negative skim milk reaction | |
| Nitrate reduction | |
| Catalase positive | |
| Phosphatase positive | |
| Urease negative | |
| Antibiotic sensitivity pattern | |
| Carbon Utilization | |
| Gelatin liquefaction | |

The morphology and growth characteristics of the *S. fradiae* E2724.1 and NRRL 12171 strains are compared in Table 4. In the tables which follow the antibiotic sensitivities (Table 5), carbon utilization (Table 6) and miscellaneous physiological characteristics (Table 7) are compared.

TABLE 4

| Growth Characteristics and Morphology | | | |
|---|---|---|---|
| | | E2724.1 | NRRL 12171 |
| Sporophores | | RA | RA |
| Spore chains | | >10 | >10 |
| Spore surface[1] | | smooth | smooth |
| Spore shape | | spherical | spherical |
| ISP#2 | G[2] | good | fair |
| | R | 87. m. yellow[3] | 87. m. yellow |
| | Am | good 263. white | none |
| | Sp | none | none |
| ISP#3 | G | poor | no growth |
| | R | 263. white | — |
| | Am | poor 263. white | — |

TABLE 4-continued

| Growth Characteristics and Morphology | | | |
|---|---|---|---|
| | | E2724.1 | NRRL 12171 |
| ISP#4 | Sp | none | — |
| | G | abundant | good |
| | R | 87. m. yellow | 87. m. yellow |
| | Am | abundant 263. white | good 92. y. white |
| ISP#5 | Sp | none | none |
| | G | good | good |
| | R | 86.1. yellow | 86.1 yellow |
| | Am | good 92. y. white | trace 93. y. gray |
| ISP#7 | Sp | none | none |
| | G | abundant | good |
| | R | 87. m. yellow | 87. m. yellow |
| | Am | abundant 263. white | good 264.1 gray |
| Bennett's | Sp | none | light brown |
| | G | poor | no growth |
| | R | 90. gy. yellow | — |
| | Am | none | — |
| Ca-malate | Sp | none | — |
| | G | good | poor |
| | R | 263. white | 92. y. white |
| | Am | good 263. white | none |
| Czapek's | Sp | none | none |
| | G | good | good |
| | R | 87. m. yellow | 87. m. yellow |
| | Am | abundant 263. white | good 92. y. white |
| Glucose-asparagine | Sp | none | none |
| | G | no growth | no growth |
| | R | — | — |
| | Am | — | — |
| | Sp | — | — |
| Tomato paste-oatmeal | G | abundant | good |
| | R | 92. y. white | 87. m. yellow |
| | Am | abundant 263. white | none |
| | Sp | none | none |

[1]Spore-surface ornamentation was determined using a scanning electron microscope.
[2]G = Growth; R = Reverse or underside of colony; Am = Aerial mycelium; Sp = soluble pigment
[3]Color names were assigned using the ISCC-NBS color charts (K. L. Kelly and D. B. Judd, "The ISCC-NBS Centroid Color Charts Standard Sample No. 2106," U.S. Dept. of Commerce, National Bureau of Standards, Washington, D. C. 20234)

TABLE 5

| Antibiotic Sensitivity[a, b] | | | | |
|---|---|---|---|---|
| Antibiotic | Conc. | Class Compound | E2724.1 | NRRL 12171 |
| Chloramphenicol | μg | nitrophenyl compound | + | + |
| Erythromycin | 15 μg | macrolide | tr | + |
| Cephaloridine | 30 μg | βlactam | + | + |
| Lincomycin | 2 μg | lincosaminide | — | — |
| Polymyxin B | 300 units | peptide | tr | tr |
| Streptomycin | 10 μg | aminoglycoside | + | + |
| Tetracycline | 30 μg | tetracycline | + | + |
| Vancomycin | 30 μg | glycopeptide | + | + |

[a]Determined by using sensitivity discs padded onto seeded-agar plates.
[b]— = resistance (no zones of inhibition)
+ = sensitivity (zones of inhibition)
tr = trace of sensitivity

TABLE 6

| Carbon Utilization[a, b] | | |
|---|---|---|
| Carbon Source | E2724.1 | NRRL 12171 |
| Control: no carbon | — | — |
| Control: Glucose | + | + |
| L-Arabinose | — | — |
| D-Fructose | + | + |
| D-Galactose | + | + |
| i-Inositol | + | + |
| D-Mannitol | — | — |
| Raffinose | — | — |
| Salicin | — | — |
| Sucrose | + | + |
| D-Xylose | + | + |

TABLE 6-continued

| Carbon Utilization[a, b] | | |
|---|---|---|
| Carbon Source | E2724.1 | NRRL 12171 |
| D-Rhamnose | — | — |

[a]— = no utilization
+ = utilization
[b]Determined on International Streptomyces Project (ISP) #9 (carbon-utilization agar) basal medium to which filter-sterilized carbon sources were added to equal a final concentration of 1.0%. Plates were incubated at 30° C. and obsered after 7 and 12 days.

TABLE 7

| Miscellaneous Physiological Characteristics | | |
|---|---|---|
| | E2724.1 | NRRL 12171 |
| ISP#1 (chromogenicity) | — | — |
| ISP#6 (chromogenicity) | — | — |
| ISP#7 (chromogenicity) | — | — |
| Gelatin liquefaction | — | — |
| Skim-milk reaction | — | — |
| pH growth range[1,2] | 6.1–8.8 | 6.1–7.8 |
| Temperature growth range[1,3] | 10–37° C. | 10–30° C. |
| NaCl tolerance[1,4] | 8% | 4% |
| Starch hydrolysis[5] | + | + |
| Nitrate reduction | + | + |
| Catalase[6] | + | + |
| Phosphatase[6] | + | + |
| Urease[6] | — | — |

[1]On ISP#2 (yeast extract-malt extract agar) medium; incubated 7 days
[2]Determined using the following buffers at a concentration of 0.05 M: citric acid, pH 3, 4, 5; 2-(N-morpholino)ethanesulfonic acid, pH 6; 3-(N-morpholino)propanesulfonic acid, pH 7; N-2-hydroxyethylpiperazine-N'-2-ethanesulfonic acid, pH 8; 2-amino-2-(hydroxymethyl)-1,3-propane-diol, pH 9; 3-cyclohexylamino-1,1-propanesulfonic acid, pH 10, 11. The pH of the agar after seven days' incubation was taken as the correct value since some of the buffers failed to hold their adjusted pH. Buffer toxicity was tested by adjusting all the buffers to pH 7.0 and determining growth. No toxicity was noted.
[3]Tested at 5, 10, 15, 20, 25, 30, 37, 40, 45, 50 and 55° C.
[4]Measured by adding NaCl to the agar to equal: 0, 2, 4, 6, 8, 10 and 12% NaCl by weight
[5]Starch hydrolysis was determined by testing for the presence of starch with iodine on ISP#4 (inorganic salts-starch agar) plates
[6]The methods of Blazevic and Ederer were followed for the enzyme assays (D. J. Blazevic and G. M. Ederer, "Principles of Biochemical Tests in Diagnostic Microbiology," John Wiley and Sons, New York, N.Y., 1975).

Based on the foregoing characteristics the organism which produces DMOT and dihydro-DMOT, NRRL 12171, is classified as a new strain of *Streptomyces fradiae*. This new culture has been deposited and made part of the stock culture collection of the Northern Regional Research Center, Agricultural Research, North Central Region, 1815 North University Street, Peoria, Illinois, 61604, from which it is available to the public under the accession number NRRL 11271.

As is the case with other organisms, the characteristics of *Streptomyces fradiae* NRRL 12171 are subject to variation. For example, recombinants, mutants or artificial variants of the NRRL 12171 strain may be obtained by treatment with various known physical and chemical mutagens, such as ultraviolet light, X-rays, gamma rays, and N-methyl-N'-nitro-N-nitrosoguanidine. All natural and artificial variants, mutants and recombinants of *Streptomyces fradiae* NRRL 12171 which retain the characteristic of DMOT production may be used in this invention.

Activity of the DMOT Compounds

The DMOT compounds inhibit the growth of pathogenic bacteria, especially gram-positive bacteria and Mycoplasma species. For example, Table 8 summarizes the minimal inhibitory concentrations (MIC), as measured by standard agar-dilution assays, at which DMOT (free base) inhibits certain bacteria.

TABLE 8
In Vitro Activity of DMOT Free Base

| Organism | MIC (μg/ml) |
| --- | --- |
| Streptococcus pyogenes C203 | 0.25 |
| Streptococcus pneumoniae Park I | 0.13 |
| Streptococcus sp. (Group D) 282 | 0.5 |
| Staphylococcus aureus 3055 | 1.0 |
| Pasteurella multocida | 6.25 |
| Pasteurella hemolytica | 25.00 |
| Mycoplasma gallisepticum | 0.097 |
| Mycoplasma hyopneumoniae | 0.39 |
| Mycoplasma hyorhinis | 0.78 |

The DMOT compounds have shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233–235 (1961)]. An $ED_{50}$ value observed for DMOT is given in Table 9.

TABLE 9
$ED_{50}$ Value of DMOT[a]

| Test Compound | Streptococcus pyogenes C203 |
| --- | --- |
| DMOT Free Base | 6.3 |
| Bacterial Challenge (X $LD_{50}$) | 268 |

[a]Subcutaneous; mg/kg × 2

For the prevention or treatment of Mycoplasma infections in poultry, an effective non-toxic amount of a DMOT compound is administered to birds orally or parenterally. DMOT compounds are most conveniently administered with a pharmaceutically acceptable carrier, such as the water ingested by the birds.

In order to illustrate more fully the operation of this invention, the following examples are provided:

EXAMPLE 1

A. Shake-flask Fermentation of DMOT

A lyophilized pellet of *Streptomyces fradiae* NRRL 12171 is dispersed in 1–2 ml of sterilized water. A portion of this solution (0.5 ml) is used to inoculate a vegetative medium (150 ml) having the following composition:

| Ingredient | Amount (%) |
| --- | --- |
| Corn steep liquor | 1.0 |
| Yeast extract | 0.5 |
| Soybean grits | 0.5 |
| CaCO$_3$ | 0.3 |
| Soybean oil(crude) | 0.45 |
| Deionized water | 97.25 |

Alternatively, a vegetative culture of *S. fradiae* NRRL 12171 preserved, in 1-ml volumes, in liquid nitrogen is rapidly thawed and used to inoculate the vegetative medium. The inoculated vegetative medium is incubated in a 500-ml Erlenmeyer flask at 29° C. for about 48 hours on a closed-box shaker at about 300 rpm.

This incubated vegetative medium (0.5 ml) is used to inoculate 7 ml of a production medium having the following composition:

| Ingredient | Amount (%) |
| --- | --- |
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DMOT

In order to provide a larger volume of inoculum, 60 ml of incubated vegetative medium, prepared in a manner similar to that described in section A, is used to inoculate 38 L of a second-stage vegetative growth medium having the following composition:

| Ingredient | Amount (%) |
| --- | --- |
| Corn steep liquor | 1.0 |
| Soybean oil meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |
| Adjust pH to 8.5 with 50% NaOH solution. | |

This second-stage vegetative medium is incubated in a 68-liter tank for about 47 hours at 29° C.

Incubated second-stage medium (4 L) thus prepared is used to inoculate 40 liters of sterile production medium having the following composition:

| Ingredient | Amount (%) |
| --- | --- |
| Fish meal | 0.9188 |
| Corn meal | 1.575 |
| Corn gluten | 0.9188 |
| CaCO$_3$ | 0.210 |
| NaCl | 0.105 |
| (NH$_4$)$_2$HPO$_4$ | 0.042 |
| Beet molasses | 2.10 |
| Soybean oil (crude) | 3.15 |
| Lecithin | 0.0945 |
| Water | 90.8859 |
| Adjust pH to 7.2 with 50% NaOH solution. | |

The inoculated production medium is allowed to ferment in a 68-liter tank for about 5 days at a temperature of 28° C. The fermentation medium is aerated with sterile air to keep the dissolved oxygen level between about 30% and 50% and is stirred with conventional agitators at about 300 rpm.

EXAMPLE 2

Isolation of DMOT

Fermentation broth, obtained as described in Example 1, and having a pH of 7.2, is filtered using a filter aid. Ethyl acetate (400 ml) is added to the filtrate (1450 ml). The pH of the solution is adjusted to 9.1 by the addition of sodium hydroxide. The solution is stirred 10 minutes, and the ethyl acetate is separated (filtering through a filter aid to clear any emulsion which forms). The filtrate is again extracted with ethyl acetate (200 ml).

Water (200 ml) is added to the combined ethyl acetate extracts; the pH of this solution is adjusted to 4.1 with phosphoric acid. After extraction, the aqueous phase is separated, and the organic phase is discarded. The aqueous phase is adjusted to pH 9.1 with sodium hydroxide and then concentrated to a volume of about 100 ml under vacuum. An amorphous precipitate forms. After permitting the precipitate to stand overnight, it is separated by filtration. The precipitate is dissolved in acetone (20 ml); water (75 ml) is added. The solution is concentrated under vacuum to remove acetone. The precipitate which forms is separated by filtration and washed with water to give about 500 mg of DMOT (1). An additional 260 mg is obtained in a similar manner from the filtrate.

EXAMPLE 3

Preparation of DOMT

DMOT (11 g), prepared as described in Example 2, is dissolved in a dilute hydrochloric acid solution (HCl added to water until the pH of the solution is 1.8). The resulting solution is allowed to stand for 24 hours at room temperature and then is adjusted to pH 9.0 by addition of sodium hydroxide. This basic solution is extracted with chloroform. The chloroform extract is dried under vacuum to give 9.65 g of DOMT (3).

EXAMPLE 4

Preparation of Dihydro-DMOT

DMOT (50 mg), prepared as described in Example 2, is dissolved in an aqueous isopropyl alcohol solution (approximately 40%; 25 ml). Sodium borohydride (20 mg) is dissolved in a 30% aqueous isopropyl alcohol solution (10 ml). The NaBH$_4$ solution (1 ml) is added to the solution containing DMOT. The resulting mixture is stirred for 5 minutes, is adjusted to pH 7.5 with phosphoric acid, and is concentrated under vacuum to remove the isopropyl alcohol. Chloroform (50 ml) is added. The pH of the aqueous phase is adjusted to 7.5. After extraction, the chloroform is separated and evaporated to dryness under vacuum to give dihydro-DMOT.

EXAMPLE 5

Preparation of Dihydro-DOMT

Dihydro-DMOT, prepared as described in Example 4, is treated in the manner described in Example 3 to give dihydro-DOMT.

EXAMPLE 6

Alternative Preparation of DOMT

DOMT is prepared from DMOT by treating DMOT in the fermentation broth in which it is produced with mild acid as described in Example 3. Isolation of DOMT is accomplished by a procedure similar to that described for DMOT in Example 2.

EXAMPLE 7

2'-O-Propionyl-DMOT

DMOT is dissolved in acetone and treated with 1.2 equivalents of propionic anhydride at room temperature for about six hours to give 2'-O-propionyl-DMOT.

EXAMPLES 8-10

2'-O-Isovaleryl-DMOT, prepared according to the procedure of Example 7, but using isovaleric anhydride.

2'-O-Benzoyl-DMOT, prepared according to the procedure of Example 7, but using benzoic anhydride.

2'-O-(n-Butyryl)DMOT, prepared according to the procedure of Example 7, but using n-butyric anhydride.

We claim:

1. A compound selected from the group consisting of (1) 23-de(mycinosyloxy)tylosin which has the structure:

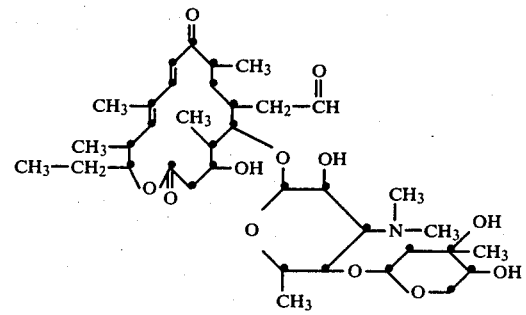

and (2) the acid addition salts of 23-de(mycinosyloxy)-tylosin.

2. The compound of claim 1 which is 23-de(mycinosyloxy)tylosin.

3. The salts of claim 1 which are pharmaceutically acceptable.

4. The salt of claim 3 which is 23-de(mycinosyloxy)-tylosin tartrate.

5. The salt of claim 3 which is 23-de(mycinosyloxy)-tylosin hydrochloride.

6. The salt of claim 3 which is 23-de(mycinosyloxy)-tylosin phosphate.

7. A compound selected from the group consisting of (1) 20-dihydro-23-de(mycinosyloxy)tylosin which has the structure:

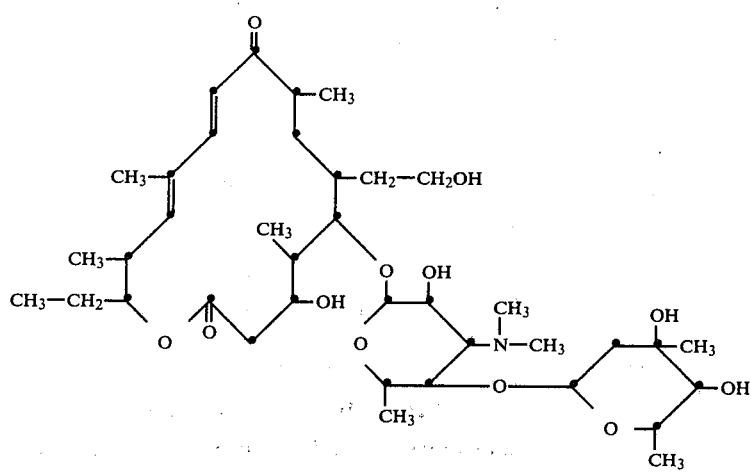

and (2) the acid addition salts of 20-dihydro-23-de(-mycinosyloxy)tylosin.

8. The compound of claim 7 which is 20-dihydro-23-de(mycinosyloxy)tylosin.

9. The salts of claim 7 which are pharmaceutically acceptable.

10. A compound selected from the group consisting of the 2'-monoesters of 23-de(mycinosyloxy)-tylosin and of 20-dihydro-23-de(mycinosyloxy)tylosin, and their acid addition salts, wherein each of said esters is an ester of a monocarboxylic acid or a hemiester of a dicarboxylic acid, each of 2 to 18 carbon atoms.

11. A compound of claim 10 which is pharmaceutically acceptable.

12. A compound of claim 11 which is a 2'-monoester of 23-de(mycinosyloxy)tylosin or an acid addition salt thereof.

13. A compound of claim 12 which is 2'-O-propionyl-23-de(mycinosyloxy)tylosin.

14. A compound of claim 12 which is 2'-O-propionyl-23-de(mycinosyloxy)tylosin tartrate.

15. A compound of claim 12 which is 2'-O-propionyl-23-de(mycinosyloxy)tylosin phosphate.

* * * * *

UNITED STATES PATENT AND TRADEMARK OFFICE
CERTIFICATE OF CORRECTION

PATENT NO. : 4,321,362

DATED : March 23, 1982

INVENTOR(S) : Richard H. Baltz, Gene M. Wild, and Eugene T. Seno

It is certified that error appears in the above—identified patent and that said Letters Patent is hereby corrected as shown below:

Column 14, lines 42-45, that portion of the structural formula reading

" 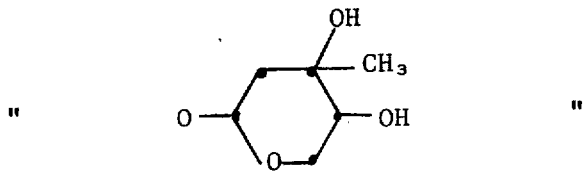 "

should read

-- 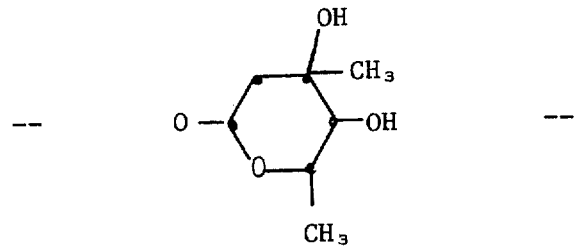 --

UNITED STATES PATENT AND TRADEMARK OFFICE
CERTIFICATE OF CORRECTION

PATENT NO. : 4,321,362

DATED : March 23, 1982

INVENTOR(S) : Richard H. Baltz, Gene M. Wild, and Eugene T. Seno

It is certified that error appears in the above—identified patent and that said Letters Patent is hereby corrected as shown below:

Column 15, line 28, "de(mycinosyloxy)-tylosin" should read -- de(mycinosyloxy)tylosin --.

Signed and Sealed this

Twenty-ninth Day of November 1983

[SEAL]

Attest:

Attesting Officer

GERALD J. MOSSINGHOFF

Commissioner of Patents and Trademarks